United States Patent [19]
Sarstedt

[11] Patent Number: 6,077,442
[45] Date of Patent: Jun. 20, 2000

[54] AUTOMATICALLY PRESSING A FILTER INTO A BLOOD-COLLECTION TUBE

[75] Inventor: Walter Sarstedt, Nümbrecht, Germany

[73] Assignee: Sarstedt AG & Co., Numbrecht, Germany

[21] Appl. No.: 08/972,182

[22] Filed: Nov. 18, 1997

[30] Foreign Application Priority Data

Nov. 19, 1996 [DE] Germany ............................ 196 47 674

[51] Int. Cl.<sup>7</sup> ....................................................... C02F 1/00
[52] U.S. Cl. .............................. 210/741; 210/86; 210/90; 210/91; 210/95; 210/97; 210/744; 210/745; 210/780
[58] Field of Search ............................ 210/359, 97, 104, 210/90, 86, 744, 741, 745, 780, 85, 91, 94, 95, 350

[56] References Cited

U.S. PATENT DOCUMENTS

| | | | |
|---|---|---|---|
| 4,021,352 | 5/1977 | Sarstedt | 210/359 |
| 4,057,499 | 11/1977 | Buono . | |
| 4,602,995 | 7/1986 | Cassaday et al. | 210/120 |
| 4,828,716 | 5/1989 | McEwen et al. | 210/740 |

*Primary Examiner*—W. L. Walker
*Assistant Examiner*—Terry K. Cecil
*Attorney, Agent, or Firm*—Herbert Dubno; Andrew Wilford

[57] ABSTRACT

A filter is pressed down in a collection tube holding separated blood as a lower solids mass and an upper liquid mass defining with the lower mass an interface. The filter has a sleeve fittable in the tube and having a lower end covered by a membrane that fits snugly in the tube. A vertical level of an upper surface of the upper liquid mass in the tube is detected and a pusher is engaged with an upper end of the sleeve to push the filter downward in the tube. Downward pushing of the filter is stopped when the upper end of the sleeve is at a predetermined spacing above the vertical level of the liquid upper surface. A vertical level of the interface is also detected and downward pushing of the filter is also stopped when the membrane is at the vertical level of the interface. Thus two separate events can trigger stopping of the downward pushing: reaching the interface or reaching a certain fill level in the sleeve.

3 Claims, 2 Drawing Sheets

AUTOMATICALLY PRESSING A FILTER INTO A BLOOD-COLLECTION TUBE

FIELD OF THE INVENTION

The present invention relates to a method of automatically pressing a filter into a blood-collection tube. More particularly this invention concerns centrifuge tubes as used for blood in high-pressure liquid chromatography (HPLC).

BACKGROUND OF THE INVENTION

In collecting blood for HPLC and other procedures as described in U.S. Pat. No. 4,057,499 of Buono, it is standard to centrifuge the blood in a standard tube having a closed lower end and a cylindrical upper portion. The whole blood is separated into the heavier solids in the lower closed end of the collection tube and a lighter liquid phase above it, normally separated at a clearly visible interface as the solids are normally opaque while the serum is clear. A separator or gel layer may lie at this interface.

A piston-like filter is used to further separate the blood solids, mainly cells, from the liquid phase, the serum or plasma. This filter fits in the collection tube with slight clearance and comprises a cylindrically tubular sleeve that fits in the tube and that carries on its lower end a porous membrane of an outside diameter that is slightly greater than the inside diameter of the collection tube. As the filter is pushed down in the collection tube the membrane forms a seal with the inner surface of the tube and allows air out as it is pushed down into contact with the surface of the serum floating atop the mass of solids. Once in contact with the liquid, the serum passes up through the filter, which might have a 0.2 μm or 0.45 μm pore size, leaving nothing but pure testable liquid in the chamber of the filter above the membrane.

Normally the sleeve of the filter is fairly short so that it can be advanced completely below the rim of the collection tube, and a cylindrical pusher that snugly fits in the collection tube is used to push it down. This is typically done manually with an operator watching that the membrane is stopped before it reaches the interface.

So long as the operator works carefully this procedure is relatively efficient. Problems occur when, for example, the filter membrane is pushed past the solid/liquid interface, contaminating the bottom of the filter with these particles. In addition when the sample has a high proportion of serum, the filter is sometimes pushed down so much that the liquid phase overflows the top of the filter sleeve, contaminating the pusher and generally making a mess so that when the filter is raised out of the centrifuge tube it sheds drips that can contaminate the workplace or other samples. It is very difficult for the operator to determine the upper surface level of the liquid when the filter is in place so overflowing it is very had to avoid with blood having a low solids content.

OBJECTS OF THE INVENTION

It is therefore an object of the present invention to provide an improved method of pressing a filter into a blood-collection tube.

Another object is the provision of such an improved method of pressing a filter into a blood-collection tube which overcomes the above-given disadvantages, that is which ensures that the filter will be only pressed down enough to obtain a clean sample.

SUMMARY OF THE INVENTION

A filter is pressed down in a collection tube holding separated blood as a lower solids mass and an upper liquid mass defining with the lower mass an interface. The filter has a sleeve fittable in the tube and having a lower end covered by a membrane that fits snugly in the tube. A vertical level of an upper surface of the upper liquid mass in the tube is detected and a pusher is engaged with an upper end of the sleeve to push the filter downward in the tube. Downward pushing of the filter is stopped when the upper end of the sleeve is at a predetermined spacing above the vertical level of the liquid upper surface. A vertical level of the interface is also detected and downward pushing of the filter is also stopped when the membrane is at the vertical level of the interface. Thus two separate events can trigger stopping of the downward pushing: reaching the interface or reaching a certain fill level in the sleeve.

According to the invention the vertical level of the interface is detected optically, by a simple electric-eye system. It can also be detected by monitoring pressure exerted on the filter as it is pushed downward, that is by monitoring fluid pressure in a pneumatic or hydraulic actuator or current consumption of an electric motor. In either case the vertical level of the upper surface is detected optically.

With this system, therefore, the filter is never pushed down into the blood solids in the bottom of the tube. In addition it is never pushed down so far that the liquid flows up over the top of the filter and contacts the pusher. Thus the equipment can be completely automated, pushing each filter down just the right amount that a good clean sample of the liquid can be taken. Once the controller operating the actuator that pushes down the filter has determined the vertical level of the upper surface of the liquid, it can control advance of the filter without actually further monitoring this level. Of course the controller is set to compensate for the additional volume of the filter when calculating where the upper liquid level actually lies once the filter is pushed down in the collection tube.

BRIEF DESCRIPTION OF THE DRAWING

The above and other objects, features, and advantages will become more readily apparent from the following description, reference being made to the accompanying drawing in which.

SPECIFIC DESCRIPTION

Figure 2:
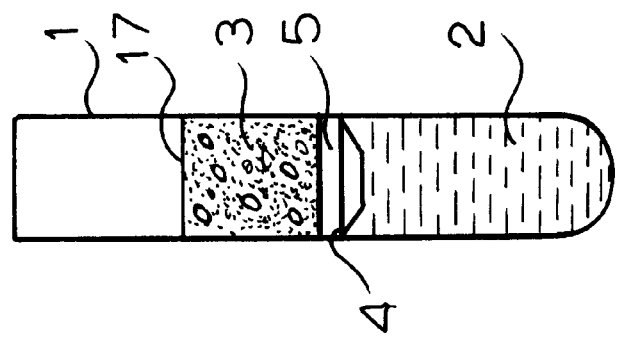
FIG. 2 is a view like FIG. 1 but showing such a tube provided with a separator.
Figure 1:
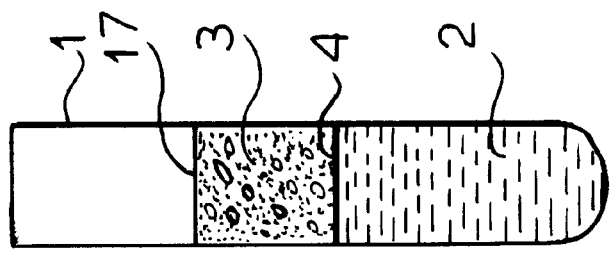
FIG. 1 is a side view of a blood-collection tube after centrifuging.

As seen in FIG. 1 a standard blood-collection/centrifuge tube 1 holds after separation a lower mass 2 of blood solids, mainly cellular matter, and an upper mass 3 of liquid, normally serum or plasma, separated from each other at an interface 4. FIG. 2 shows how a standard separator 5 may be provided at the interface 4 and in FIG. 3 a layer 6 of gel lies at the interface 4. The serum 3 has an upper surface 17.

Figure 3:
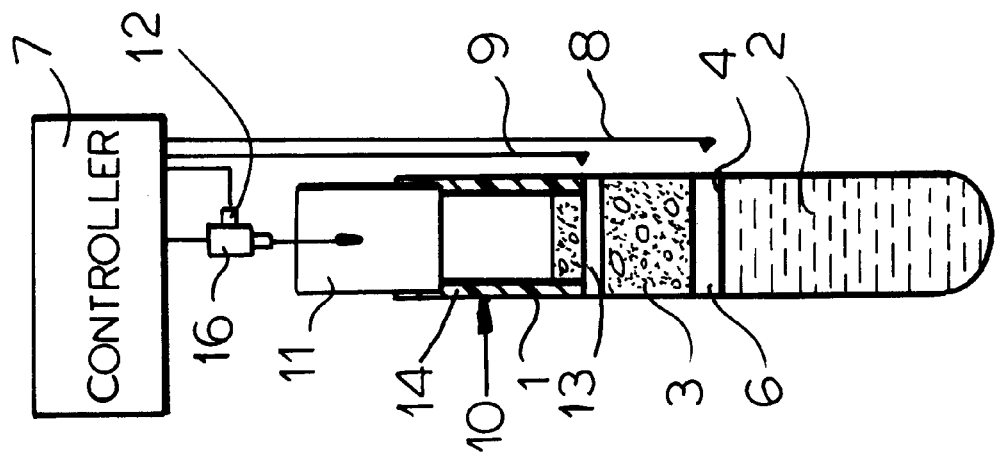
FIG. 3 is a partly schematic side view illustrating the method of this invention in a starting phase.

FIG. 3 further shows how according to the invention a sensor 8 is provided which can optically detect the vertical position of the interface 4, here formed by the gel layer 6, and another sensor 9 is provided which can similarly detect the upper surface 17 of the liquid phase 1. Both sensors can be simple electric-eye arrays and can in fact both be part of a single vertically extending such array.

A filter 10 comprises a cylindrically tubular sleeve 14 of an outside diameter equal to slightly less than the inside diameter of the tube 1 and at its open lower end a filter membrane 13 of the desired porosity and having an outside diameter equal to or slightly more than the inside diameter of the tube 1. Thus the filter 10 fits like a piston inside the tube 1. The length of the sleeve 14 is substantially less than the distance between the upper surface 17 of the serum 3 and the rim or mouth of the tube 1 so that it is fitted therein and then pressed down by a cylindrical pusher 11. Normally the pusher 11 is rammed down manually by an operator.

According to the invention, however, the pusher 11 is pressed axially down in the tube 1 by an actuator 16 operated in turn by a controller 7. This controller 7 is also provided with the sensor 8 that can detect the vertical level of the interface 4, the sensor 9 that can detect the vertical level of the upper surface 17 of the serum 3, and a sensor 12 that can detect the amount of force the actuator 16 is bringing to bear on the pusher 11 to advance it downward.

Figure 5:
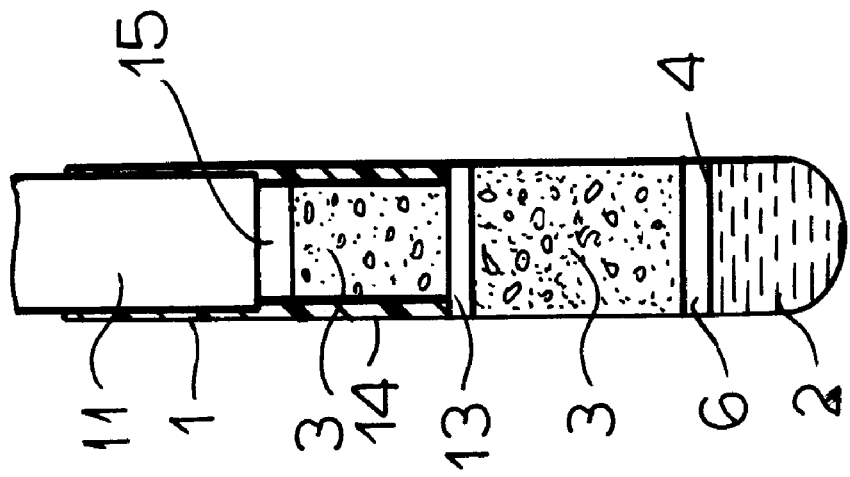
FIG. 5 is a view like FIG. 4 showing an ending phase under different circumstances.
Figure 4:
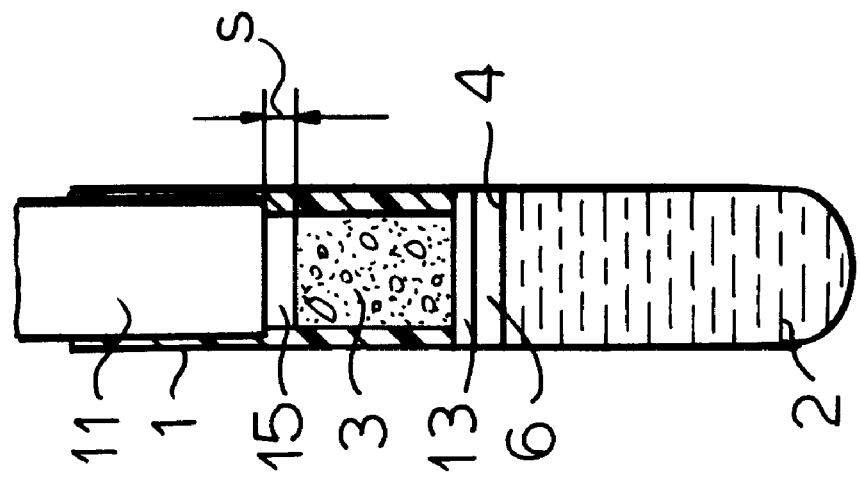
FIG. 4 is a view like FIG. 3 but showing the method in the ending phase.

Thus the system of this invention can work in several ways. After ascertaining the level of the interface 4 and the upper surface 17, the pusher 11 is advanced until either the filter membrane 13 on its lower end reaches the interface or the upper surface 17 level comes within a spacing s of the upper end of the sleeve 14, as shown in FIG. 4. As a result the membrane 13 will never contact the actual solids 2 in the base of the tube 1 and at the same time it will never advance so far that the serum will overflow the top of the sleeve 14. FIG. 5 shows how the filter 13 is stopped well above the interface at the gel layer 6 in blood having a low solids content, leaving an empty space 15 at the top of the filter 10 and substantial spacing between the lower end of the filter 10 and the interface 4.

Instead of relying on the output of the interface sensor 8, the controller 7 can monitor the pressure being exerted by the actuator 16. This pressure rises precipitously when the interface 4 is reached, so that in this case the controller 7 will stop advance as soon as this precipitous pressure increase is detected. Of course this works together with the surface sensor 9 to prevent the sleeve 14 from overflowing so as always to leave the empty space 15 in the sleeve 14 above the filtered liquid therein.

I claim:

1. A method of pressing into a collection tube holding separated blood as a lower solids mass and an upper liquid mass defining with the lower mass an interface a filter comprising a sleeve fittable in the tube and having a lower end covered by a membrane that fits snugly in the tube, the method comprising the steps of:

monitoring a vertical position of an upper surface of the upper liquid mass in the tube;

engaging a pusher with an upper end of the sleeve and pushing the filter downward in the tube so as to force the liquid mass upward through the filter into the sleeve;

stopping downward pushing of the filter when the upper end of the sleeve is at a predetermined spacing above the current vertical position of the liquid upper surface;

is monitoring pressure exerted on the filter as it is pushed downward and thereby determining a vertical position of the interface; and stopping downward pushing of the filter when the membrane is at the vertical position of the interface.

2. The method defined in claim 1 wherein the vertical position of the interface is detected optically.

3. A method of pressing into a collection tube holding separated blood as a lower solids mass and an upper liquid mass defining with the lower mass an interface a filter comprising a sleeve fittable in the tube and having a lower end covered by a membrane that fits snugly in the tube, the method comprising the steps of:

monitoring a vertical position of an upper surface of the upper liquid mass in the tube and feeding an output corresponding thereto to a controller;

engaging a pusher with an upper end of the sleeve and pushing the filter by means of the controller downward in the tube so as to force the liquid mass upward through the filter into the sleeve;

stopping downward pushing of the filter by means of the controller when the upper end of the sleeve is at a predetermined spacing above the current vertical position of the liquid upper surface;

monitoring pressure exerted on the filter as it is pushed downward and thereby determining a vertical position of the interface and feeding an output corresponding thereto to the controller; and stopping downward pushing of the filter by means of the controller when the membrane is at the vertical position of the interface.

* * * * *